United States Patent [19]

Sano et al.

[11] Patent Number: 5,665,539
[45] Date of Patent: Sep. 9, 1997

[54] IMMUNO-POLYMERASE CHAIN REACTION SYSTEM FOR ANTIGEN DETECTION

[75] Inventors: Takeshi Sano; Charles R. Cantor; Cassandra L. Smith, all of Boston, Mass.

[73] Assignee: The Regents of the University of California, Oakland, Calif.

[21] Appl. No.: 131,301

[22] Filed: Oct. 4, 1993

Related U.S. Application Data

[63] Continuation-in-part of Ser. No. 729,460, Jul. 12, 1991, Pat. No. 5,328,985.

[51] Int. Cl.$^6$ ............................................. C12Q 1/66
[52] U.S. Cl. ........................... 435/6; 435/7.1; 435/7.2; 435/7.5; 435/7.8
[58] Field of Search .................... 435/7.1, 69.1, 435/252.3, 320.1, 6, 7.5, 7.8; 530/350, 387.1; 536/22.1, 23.1, 23.2, 23.4, 23.7

[56] References Cited

U.S. PATENT DOCUMENTS

| | | | |
|---|---|---|---|
| 4,478,914 | 10/1984 | Giese | 428/407 |
| 4,839,293 | 6/1989 | Cantor et al. | 435/320 |
| 5,100,788 | 3/1992 | Löfdahl | 435/69.7 |
| 5,109,124 | 4/1992 | Ramachandran | 536/27 |
| 5,168,049 | 12/1992 | Meade | 435/69.1 |

FOREIGN PATENT DOCUMENTS

| | | |
|---|---|---|
| 135532 | of 0000 | European Pat. Off. |
| 84900773.7 | 2/1984 | European Pat. Off. |
| 8501901 | 10/1985 | WIPO |
| WO8602077 | 4/1986 | WIPO |
| WO8802776 | 4/1988 | WIPO |
| WO8809344 | 12/1988 | WIPO |
| WO8909393 | 10/1989 | WIPO |

OTHER PUBLICATIONS

*Journal of Clinical Microbiology*, Sep. 1990, pp. 1968–1973, Diagnosis of *Chlamydia trachomatic* Cervical Infection by Detection of Amplified DNA with an Enzyme Immunoassay, Linda Bobo, Francois Coutlee, Robert H. Yolken, Thomas Quinn, and Raphael P. Viscidi.

*Science*, vol. 258, 2 Oct. 1992, "Immuno–PCR: Very Sensitive Antigen Detection by Means of Specific Antibody–DNA Conjugates," Takeshi Sano, Cassandra L. Smith, Charles R. Cantor.

Syvanen et al. Nucleic Acids Research 16(23):11327–11338 1988.

Argarana, C.E.; Konty, D.D.; Birken, S.; Axel, R.; Cantor, C.R., Molecular Cloning and Nucleotide Sequence of the Streptavidin Gene, *Nuc. Acids. Res.*, 14:1871–1887 (1986).

Sano, T., Cantor, C.R. Expression of a Cloned Streptavidin Gene in *Escherichia Coli*, Proc. Nat. Acad. Sci., 87:142–146 (1990).

Sano, T., Cantor, C.R. Expression Vectors for Streptavidin-containing Chimeric Proteins, Bioch. Biophys. Res. Comm., 176:571–577 (1991).

Surolia, A., Pain, D., Khan, M.I., Protein A: Nature's Universal Antibody, Trends Biol. Sic., pp. 74–76, (Feb. 1982).

Sano, T., Cantor, C.R., Cooperative Biotin Binding by Streptavidin, J. Biol. Chem., 265: 3369–3373 (1990).

(List continued on next page.)

*Primary Examiner*—Keith C. Furman
*Attorney, Agent, or Firm*—Richard Aron Osman

[57] ABSTRACT

A novel system and method for sensitive antigen detection. The system utilizes immuno-polymerase chain reaction in which a specific biotinylated nucleic acid molecule is used as the marker. The biotinylated marker is attached to antigen-antibody complex through a streptavidin-protein A chimeric protein that possesses tight and specific binding affinity both for biotin and immunoglobulin G. A segment of the attached biotinylated marker is amplified by polymerase chain reactions with appropriate primers and the polymerase chain reaction products are detected by agarose gel electrophoresis. The method can detect any antigen and has a greater sensitivity than any existing antigen detection system.

14 Claims, 1 Drawing Sheet

OTHER PUBLICATIONS

Bayer, E.A., Ben-Hur H., Wichek, M., Isolation and Properties of Streptavidin, Meth. Enzym., 184: 80–89 (1990).

Green, M.N., Avidin and Streptavidin, Meth. Enzym., 184: 51–67 (1990).

Lowenadler, B.; Nilsson, B.; Abrahmsen, L.; Moks, T.; Ljunggvist, L.; Holmgren, E.; Paleus, S.; Josephson, S.; Philipson, L.; Uhlen, M. Production of Specific Antibodies Against Protein A Fusion Proteins, E.M.B.O. J 5:2393–2398 (1986).

Sano, T.; Cantor, C.R., A Streptavidin–Protein A Chimera that Allows One-step Production of a Variety of Antibody Conjugates, Bio/Technology, 9:1378–1381 (1991).

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
　　　　( A ) LENGTH: 30 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO: 1:

ATTGTTGCCG GGAAGCTAGA GTAAGTAGTT　　　　　　　　　　　30

( 2 ) INFORMATION FOR SEQ ID NO:2:

-continued

```
( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 2:

GAGATTTATG CAGTGCTGCC ATAACCATGA                                    30
```

IMMUNO-POLYMERASE CHAIN REACTION SYSTEM FOR ANTIGEN DETECTION

This is a continuation-in-part of the U.S. Application entitled "Recombinant Streptavidin-Protein A Chimeras Useful for Conjugation of Molecules in the Immune System", application Ser. No. 07/729,460, filed on Jul. 12, 1991 now U.S. Pat. No. 5,328,985.

This invention was made with government support under grant Contract No. CA 39782 awarded by the National Cancer Institute, National Institutes of Health. The government has certain rights in this invention.

BACKGROUND OF THE INVENTION

1. Field of the Invention

This invention concerns novel methods and systems for sensitive antigen detection.

2. Background and Related Disclosures

Attempts have been made previously to develop sensitive methods for detection of antigenic, nucleic acid containing entities. For example U.S. Pat. No. 5,077,192 relates to a method for the detection of low levels of medically important organisms such as bacteria, viruses, malignant cells and the like. The abstract of the Japanese application JP 3231151 describes detecting a modified nucleic acid recognized by an antibody added to 5'-terminal site of primer or to DNA amplified by primer. PCT 91/AU91/00131, filed on Apr. 5, 1991, describes a method for capturing target DNA from a sample, amplifying the DNA using a PCR and detecting the amplified DNA.

*J. Clin. Microbiol.*, 28:1968 (1990) describes a system for detection of amplified Chlamydia trachomatis DNA from cervical specimens by fluorometric quantitation in an enzyme immunoassay (EIA) format, which includes a polymerase chain reaction.

SUMMARY

One aspect of the current invention is a very sensitive method of detecting an antigen by:

(a) contacting said antigen with an antibody to form a first complex comprising of antigen and antibody;

(b) contacting a linker molecule having the ability to bispecifically bind to biotin and to immunoglobulin G, with a segment of biotinylated nucleic acid marker to form a second complex comprising the linker and biotinylated nucleic acid;

(c) conjugating said first complex with a second complex to form a third complex comprising the antigen-antibody-linker-biotinylated marker;

(d) specifically amplifying the nucleic acid sequence comprised within the biotinylated marker; and (e) detecting the amplified nucleic acid sequence.

Another aspect of the current invention is a method wherein a linker is protein, peptide, a streptavidin-protein A chimeric protein containing both a biotin-binding domain and an antibody-binding domain, a cross-linked marker nucleic acid-antibody or a biotinylated marker nucleic acid cross-linked to biotinylated antibody by streptavidin or avidin.

Still another aspect of the current invention is a method wherein streptavidin in the chimeric protein binds specifically to biotinylated marker through its biotin-binding domain and protein A binds specifically to the antibody through its immunoglobulin G-binding domain.

Still yet another aspect of the current invention is a method for detecting an antigen by:

(a) contacting said antigen with an antibody to form a first complex comprised of antigen and antibody;

(b) contacting linker, wherein the one side of the linker has a domain which specifically binds to biotin and the other side of the chimeric protein has a domain which specifically binds to immunoglobulin G, with a segment of biotinylated marker defined by one or more primers, to form a second complex comprising the streptavidin-protein A chimeric protein and biotinylated marker;

(c) conjugating said first complex with a second complex to form a third complex comprising biotinylated marker-biotin binding domain-antibody-antigen conjugate;

(d) amplifying the nucleic acid sequence comprised within the biotinylated marker defined by primers using a polymerase chain reaction or detecting the nucleic acid sequence by other appropriate method; and (e) detecting the amplified nucleic acid sequence.

Yet another aspect of the current invention is a composition for use in an immunoassay for antigen detection comprising a streptavidin-protein A chimeric peptide having a biotin-binding domain and an immunoglobulin G-binding domain, and an amplifiable, biotinylated polynucleic acid of predetermined sequence bound to said chimeric protein through binding of biotin to said biotin-binding domain.

Still another aspect of the current invention is a composition for use in an immunoassay, comprising a peptide or protein having an antibody-binding domain and an amplifiable polynucleic acid bound to said peptide.

Still another aspect of the current invention is a composition for detection of any antigen, particularly those selected from the group consisting of proteins, peptides, lipids, carbohydrates, nucleic acid, haptens and their derivatives and analogues, wherein a peptide or protein comprises both a biotin-binding domain and also an immunoglobulin G-binding domain and wherein the polynucleic acid is biotinylated DNA defined by a pair of primers.

DETAILED DESCRIPTION OF THE INVENTION

Figure 1:
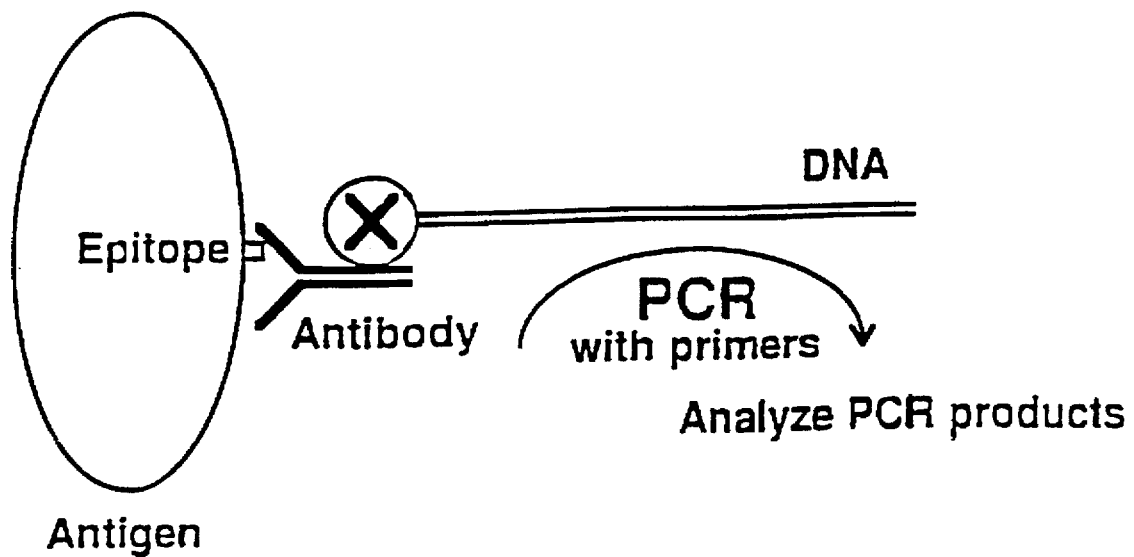
FIG. 1 is a schematic illustration of concept of immuno-polymerase chain reaction.

The invention concerns an extremely sensitive method and system for detection of antigens by means of specific antigen-antibody-marker-conjugates. The antigen detection system, called immuno-polymerase chain reaction, utilizes a specific DNA molecule as a marker and a bispecific chimeric protein as a linker between the marker molecule and the antigen to be detected while conjugated to an antibody.

There are several novel features involved in this invention. First, a nucleic acid sequence is used as the marker for detection of antigen. Second, antibody-linker-biotinylated marker conjugates are used to attach a marker molecule to an antigen. Third, enzymatic steps such as a polymerase chain reaction are used to amplify signals for detection of specific antigens. Fourth, due to the specificity and efficiency of nucleic acid amplification, the detection sensitivity of the immuno-PCR technology is superior to that of any existing antigen detection system and the method is, in principle, able to detect a single antigen molecule. No method of such sensitivity is currently available. Fifth, a wider variety of antigens can be detected by the immuno-PCR than by other currently available antigen detection systems.

Briefly, in the current invention, a linker molecule with bispecific binding affinity for nucleic acids and antibodies is used to attach a DNA, RNA, DNA/RNA hybrid, or their fragment, analogue or derivative molecule used as a marker, specifically to an antigen-antibody complex, resulting in the formation of a specific antigen-antibody-linker-DNA conjugate. A segment of the attached marker is amplified enzymatically (such as by a polymerase chain reaction with appropriate primers). The presence of specific products of polymerase chain reaction or other amplification methods demonstrates that marker molecules are attached specifically to antigen-antibody complexes and in turn, this indicates the presence of antigen.

A streptavidin-protein A chimera previously synthesized and disclosed in co-pending applications identified above was used as the linker molecule. The chimera has two independent specific binding abilities. One is its binding to biotin, derived from the streptavidin moiety, and the other is its binding to the Fc portion of an immunoglobulin G (IgG) molecule, derived from the protein A moiety. This bifunctional specificity both for biotin and antibody allows the specific conjugation of any biotinylated nucleic acid molecule to antigen-antibody complexes. Other linker molecules, such as any protein, peptide, nucleic acid marker chemically cross-linked to antibodies, or biotinylated marker nucleic acid cross-linked to biotinylated antibodies by streptavidin or avidin may be also advantageously utilized.

In the current invention, a streptavidin-protein A chimera or any other linker that possesses tight and specific binding affinity both for biotin and immunoglobulin G was used to attach a biotinylated marker specifically to antigen-monoclonal antibody complexes that had been immobilized on microtiter plate wells. Next, a segment of the attached marker was amplified by PCR. Analysis of the PCR products by agarose gel electrophoresis after staining with ethidium bromide allowed as few as 580 antigen molecules ($9.6 \times 10^{-22}$ moles) to be readily and reproducibly detected. Direct comparison with enzyme-linked immunosorbent assays (ELISA) with the use of a chimera-biotinylated alkaline phosphatase conjugate demonstrated that approximately $10^5$ times enhancement in antigen detection sensitivity was obtained with the use of immuno-PCR. Given the enormous amplification capability and specificity of PCR, the current immuno-PCR technology has a sensitivity greater than that of any existing antigen detection system and, in principle, is sensitive enough to be applied to the detection of single antigen molecules.

One mode of the immuno-PCR technology of the current invention, in which a specific antibody-DNA conjugate is used to detect antigens, utilizes immobilization of various amounts of an antigen on the surface of microtiter plate wells. For initial testing, bovine serum albumin (BSA) was used as the antigen because of the availability of both the pure protein and monoclonal antibodies against it. The detection procedure used was similar to conventional enzyme-linked immunosorbent assays (ELISA). Instead of an enzyme-conjugated secondary antibody directed against the primary antibody, as in typical ELISA, a biotinylated linear plasmid DNA (pUC19), conjugated to the streptavidin-protein A chimera, was targeted to the antigen-antibody complexes. A segment of the attached marker was amplified by PCR with appropriate primers and the resulting PCR products were analyzed by agarose gel electrophoresis after staining with the ethidium bromide.

The concept of immuno-PCR of the current invention is shown schematically in FIG. 1. By using linker molecule X which has bispecific binding affinity both for the marker for antibody, a molecule used as a marker can be specifically attached to an antibody-antigen complex. Marker molecules are typically DNA, RNA, DNA-RNA hybrids, their derivatives, fragments, segments or analogues. The attached marker allows the amplification of its segment(s) by PCR with appropriate primers. The enormous amplification capability and specificity of PCR allows the production of large amounts of specific DNA segments as PCR's products. These products can be detected by various methods known and used in molecular biology such as, for example, by agarose gel electrophoresis. The presence of specific PCR products demonstrates that marker molecules are attached to antigen-antibody complexes, indicating the presence of antigen. In addition, the quantitation of PCR products also provides the estimation of the number of antigens (epitope).

A streptavidin-protein A chimera is an ideal molecule to serve as a linker molecule X. Its bifunctional specificity both for biotin and immunoglobulin G (antibody) allows the specific conjugation of a DNA molecule to antigen-antibody complexes upon biotinylation of the DNA.

The Linker: Streptavidin-Protein A Chimera

Linker molecule can be any material which is able to specifically recognize, or which possesses both the antibody-binding domain and also the biotin-binding domain. The linker may be any protein, peptide, nucleic acid marker cross-linked to antibody or biotinylated marker nucleic acid cross-linked to biotinylated antibody by streptavidin or avidin. The most preferred linker is a recombinant streptavidin-protein A chimeric protein.

A recombinant streptavidin-protein A chimeric protein having two biological recognition specificities was used as a linker between an antigen-antibody complex and biotinylated DNA. A gene fusion of streptavidin with protein A encoding two immunoglobulin G (IgG)-binding domains was efficiently expressed in *Escherichia coli* and the expressed chimeric protein was purified to homogeneity by simple procedures well known in the art. The purified chimeric protein can bind one biotin molecule per subunit and has thus full biotin-binding ability and can also bind one or more immunoglobulin G molecules per subunit. With the specific and tight binding affinity of the streptavidin-protein A chimeric protein both for immunoglobulins and biotin, any biological material containing biotin may be conjugated and/or labeled with immunoglobulin molecules and/or such molecules may be detected. This dual ability of streptavidin-protein A chimera was utilized in the current invention to link the antigen-antibody complex with biotinylated DNA subsequently amplified by polymerase chain reaction.

Two biological recognition specificities of the streptavidin-protein A chimeric protein of the current invention are conferred on that protein by streptavidin which specifically binds biotin with extremely high affinity and by protein A which binds various antibodies, preferably IgG, with high affinity. Since biotin can be easily incorporated into various biological substances, the streptavidin-biotin system offers an avenue by which the second system, namely protein A-bound antibody, such as human or other mammalian IgG, $IgG_1$, $IgG_2$, $IgG_3$, $IgG_4$, IgM, IgA, SIgA or IgE, can be conjugated with antigens.

Streptavidin is a protein closely related to avidin. Like avidin, streptavidin was found to bind rapidly and almost irreversibly to any molecule containing biotin with specific affinity $Kd \approx 10^{-15}$ M.

Efficient expression of a cloned streptavidin gene in *Escherichia coli* using T7 expression system is described in

*Proc. Natl. Acad. Sci.*, 87:142 (1990), incorporated herein by reference. The establishment of the expression system allowed the design and preparation of streptavidin-containing chimeric proteins as those described in copending applications Ser. No. 07/729,460 now U.S. Pat. No. 5,328,985, and application Ser. No. 07/729,717 incorporated by reference. *J. Biol. Chem.*, 265:3369 (1990) describes the cooperativity of the biotin binding of streptavidin.

The Marker: Biotinylated DNA

A specific marker molecule was used as a marker in the conjugated DNA-linker-antibody-antigen complex. The marker molecule may be DNA, RNA, DNA-RNA hybrid, fragment, segment, their derivative and analogue. The marker DNA, as used in this invention, serves as the entity recognizable and amplifiable by PCR. For the purposes of this invention, the marker DNA is biotinylated. Biotinylated DNA is easily conjugated to the streptavidin moiety of the streptavidin-protein A chimera allowing a specific binding of biotinylated DNA to the chimera.

A biotinylated linear plasmid (pUC19) was used as marker DNA. The biotinylated pUC19 was a linear 2.67-kb Hind III-AccI fragment in which one biotin molecule had been incorporated at its Hind III terminus by a filling-in reaction with Sequenase version 2.0 (U.S. Biochemical) in the presence of a biotinylated nucleotide (biotin-14 deoxyadenosine triphosphate; Bethesda Research Laboratory). By gel retardation dependent on streptavidin binding, almost 100% of the 2.67 kb fragment contained biotin.

Plasmid pUC19 was purified by a standard method, and digested to completion with AccI and Hind III. The termini of the fragments were filled-in with a modified T7 DNA polymerase in the presence of a biotinylated nucleotide (biotin-14-dATP), dTTP, dGTP, and dCTP. Each of the resulting DNA fragments (2.67 kb and 21 bp) contains one biotin molecule at its Hind III terminus. The 2.67 kb fragment was precipitated with ethanol several times to remove unincorporated nucleotides and the 21 bp fragment, and used as biotinylated pUC19 to prepare a chimera-pUC19 conjugate as described below.

Conjugation of Biotinylated pUC19 to the Streptavidin-Protein A Chimera

A marker is attached to a linker by any method suitable to conjugate the marker with the linker. The most preferred method of conjugation is described below.

Biotinylated DNA and streptavidin-protein A chimeric protein were conjugated into chimera-pUC19, a biotinylated DNA-streptavidin-protein A complex.

The chimera-pUC19 conjugate was prepared by mixing the purified streptavidin-protein A chimera (1.4 pmol subunits, 44 ng) and the biotinylated pUC19(1.4 pmol, 2.5 μg). Two components were mixed at a ratio of biotin-binding site to biotin of 1:1. The resulting conjugates contain four biotinylated pUC19 per chimera, which possesses four biotin binding sites.

Conjugation of Antigen with Antibody

Any antigen to be detected is conjugated with its own specific antibody to form an antigen-antibody complex. Antibody can be monoclonal or polyclonal such as various immunoglobulins IgG, IgM, IgA, IgE and their fragments, derivatives and analogues. Antibody can be biologically or chemically produced or genetically engineered.

Any antigen can be detected by the current method as long as it conjugates with antibody which is recognizable by the linker. Antigen may be, among others, a protein, peptide, lipid, carbohydrate, nucleic acid, hapten or their derivatives.

Preparation of PCR Primers

Primers required for DNA replication by DNA polymerase chain reaction have nucleotide sequences complementary to the DNA that flanks the target region, that is, these are nucleotide sequences sequestering the DNA region under consideration. In this case, the primers flank a segment of the biotinylated DNA region.

Primers were prepared as follows. Two 30-mer primers, bla-1 and bla-2, were synthesized by β-cyanoethyl phosphoramide chemistry using an automated DNA synthesizer, and purified using NENSORB PREP cartridges (DuPont).

The sequences of the primers are:

| bla-1 - - - ATT GTT GCC GGG AAG CTA GAG | |
| TAA GTA GTT | SEQ. ID. NO. 1 |
| bla- 2 - - - GAG ATT TAT GCA GTG CTG CCA | |
| TAA CCA TGA | SEQ. ID. NO. 2 |

These primers hybridize to a segment of the bla (β-lactamase) gene, and generate a 261 bp fragment upon PCR amplification.

One, two or more primers can be used. Only one primer, for example, is sufficient to amplify a segment of marker nucleic acids, in which the primer hybridizes to two different regions of a marker nucleic acid molecule flanking the amplified segment and having the opposite direction. Two or more set of primers can be used to amplify more than one segment of attached marker nucleic acids.

Amplification of the Marker

Amplification of the marker molecule is by methods suitable for such purposes. The most preferred method is a polymerase chain reaction.

Polymerase chain reaction is the process wherein a specific segment of DNA can be amplified by more than a hundred thousand times relative to nearby nucleotide sequences. In the current invention the enormous amplification capability is used to replicate a segment of the biotinylated DNA attached specifically to streptavidin protein A chimera-antibody-antigen complexes to achieve the highest possible degree of sensitivity in antigen detection. Such high sensitivity will result from million to billion fold amplification of a segment of the biotinylated DNA which is attached specifically to the antigen to be detected.

The efficacy of PCR is based on its ability to amplify a specific DNA segment flanked by a set of primers. The enormous amplification capability of PCR allows the production of large amounts of specific DNA products, which can be detected by various methods. The extremely high specificity of PCR for a target sequence defined by a set of primers avoids the generation of false signals from other nucleic acid molecules present in samples.

The capability of antigen detection systems can be considerably enhanced and broadened by coupling to PCR.

PCR is typically carried out under the following conditions. The mixture containing 20–70, preferably 50 mM KCl, 5–20, preferably 10 mM Tris-Cl having pH 8.3, 0.5–3, preferably 1.5 mM $MgCl_2$, 10 μg/ml gelatin, 0.8 mM dNTPs (0.2 mM each), 2 μM primers (bla-1 and bla-2, 1 μM each), and 50 units/ml Taq DNA polymerase (Boehringer Mannheim), is prepared. Pre-PCR mixtures are placed in 500 μl polypropylene tubes and sterilized by UV irradiation at 254 nm for 10–50, preferably 20 minutes (4×5 minutes), using Stratalinker UV Crosslinker (Stratagene) to degrade contaminated DNA, which would generate false signals upon PCR amplification. Light mineral oil (Fisher Scientific) was sterilized in the same manner. The sterilized pre-PCR mixtures are added to the wells of a microtiter plate (40 μl/well), and the sterilized mineral oil is layered (20 μl/well) over the reaction mixture.

PCR is performed using an automated thermal cycler, (PCT-100-96 Thermal Cycler obtained from MJ Research, Inc., Watertown, Mass.) which is designed for microtiter plates, using the following temperature profile:

initial denaturation is carried out at 94° C. for 5 minutes;
denaturation is carried out at 94° C. for 1 minutes;
annealing is carried out at 58° C. for 1 minutes;
extension is carried out at 72° C. for 1 minutes;
30 cycles of amplification (denaturation-annealing-extension) are carried out;
final extension is carried out at 72° C. for 5 minutes.

Other examples of detection methods for the marker are hybridization, or detection of a label. Hybridization of a label-containing probe to attached marker DNA is performed by methods known in the art, followed by the detection of the label. Any labels, including radioisotopes, fluorochromes, chromophores, and enzymes, can be used for this purpose.

Detection of a label which has been incorporated directly into marker DNA is performed by methods known in the art. Many labels, which can be incorporated specifically into DNA, are available. They include fluorescent dyes such as for example, ethidium bromide and ethidium homodimer, which are frequently used in molecular biology. Another way is to attach a hapten such as for example, biotin and FITC, to the marker DNA, followed by the detection of the label by using, for example, antibodies against the label.

A method similar to polymerase chain reaction but without amplification is by a primer extension. A segment of attached marker DNA is synthesized by primer extension, which is one cycle reaction, and thus not a polymerase chain reaction, followed by the detection of the synthesized segment.

Detection of Antigen Immobilized on Microtiter Plate by Immuno-PCR

The current method concerns a detection of very small amounts of antigen bound by an antibody, which is conjugated to IgG-binding moiety of protein A in streptavidin-protein A chimera, which is conjugated through its biotin-binding moiety to the biotinylated DNA. A segment of the attached DNA is amplified with PCR and the PCR product is detected by agarose gel electrophoresis.

Typically, the antigen is first conjugated to the antibody to form a first complex and the biotinylated DNA is conjugated to streptavidin-protein A chimera to form a second complex. The first and the second complexes are then conjugated to form the third complex, i.e. biotinylated DNA-streptavidin-protein A chimera-antibody-antigen conjugate.

Because of the availability of pure antigen and of monoclonal antibodies against it, to develop and to test the immuno-PCR method of this invention, bovine serum albumin (BSA) was used as the antigen. The procedures for detecting BSA immobilized on a microtiter plate by immuno-PCR are described below. The detection method and assays for other antigens are run under the same or slightly modified conditions.

Various amounts (6.4 ng–6.4 ag; 96 fmol–9.6×10$^{-22}$ mol; 5.8×10$^{10}$–5.8×10$^{2}$ molecules) of BSA or other antigen in 45 μl of 150 mM NaCl, 20 mM Tris-Cl (pH 9.5), and 0.02% NaN$_3$ prepared by serial dilution, are placed in wells of a microtiter plate (Falcon 3911, polyvinyl chloride; Becton Dickinson). The microtiter plate is incubated at 2° C.–20° C., preferably at 4° C., for 6–16 hours or overnight, to immobilize BSA molecules on the surface of the wells. The same solution without BSA is used as the control.

The wells are briefly washed several times with Tris-buffered saline (TBS) consisting of 150 mM NaCl, 20 mM Tris-Cl (pH 7.5), and 0.02% NaN$_3$], and 200 μl of ETBS (TBS plus 0.1 mM EDTA) containing 4.5% non-fat dried milk and 1 mg/ml denatured DNA, such as salmon sperm DNA, are added into each well. The microtiter plate is incubated at 32° –42° C., preferably 37° C. for 40–120 minutes, preferably 80 minutes, to block reactable sites on the surface of the wells to avoid non-specific binding in subsequent steps, and then the wells are washed several times with TETBS (TBS plus 0.1 mM EDTA and 0.1% Tween 20). Into each well is added 50 μl of TETBS containing 0.45% non-fat dried milk, 0.1 mg/ml denatured salmon sperm DNA, and diluted monoclonal or polyclonal antibody. For testing of BSA antigen, 8,000-fold diluted monoclonal antibody against BSA which was mouse ascites fluid; IgG2a; clone BSA-33, obtained from Sigma, is used. The plate is incubated at 18°–26° C., preferably at room temperature (~20°C.) for 15–90 minutes, preferably for 45 minutes to allow the antibody to bind to immobilized BSA molecules. The wells are then washed extensively with TETBS to remove unbound antibody molecules, and about 50 μl of TETBS containing 0.45% non-fat dried milk, 0.1 mg/ml denatured salmon sperm DNA, and 140 amol of biotinylated pUC19 conjugated to the streptavidin-protein A chimera are added into each well. The microtiter plate is incubated at room temperature for 20–120 minutes, preferably for 60 minutes, to allow the chimera-pUC19 conjugates to bind to the antigen-antibody complexes. The wells are again washed extensively with TETBS to remove unbound conjugates and again washed briefly with TBS without NaN$_3$. The microtiter plate is subjected to PCR as described above. After the PCR amplification, each reaction mixture is analyzed by agarose gel electrophoresis. A post-PCR mixture, in amount from 10–30 μl, preferably about 15 μl, is analyzed by standard agarose gel electrophoresis, stained with ethidium bromide.

Immuno-PCR technology using a specific DNA molecule as the marker can reliably detect very small amounts of antigen with sufficient reproducibility. The sensitivity of immuno-PCR is superior to that of any existing antigen detection system. Therefore, this technology is particularly useful for detecting rare antigen molecules in biological samples. The extremely high sensitivity of immuno-PCR enables this method to detect single antigen molecules; no current method allows detection with such a degree of sensitivity. The sensitivity of immuno-PCR can be controlled by varying one or more key factors. This suggests that immuno-PCR technology can be used on a wide variety of biological samples.

Linker-Target Conjugation

In other variations of the instant method, marker nucleic acid is attached specifically to targets, not via antigen-antibody binding but by using specific binding ability of a linker. The attached marker nucleic acids are detected by polymerase chain reaction or by other appropriate methods. Examples of such linker-target pairs include receptors and their ligands, enzymes and their cofactors, enzymes and their substrates, and DNA and DNA binding proteins.

FIG. 1 illustrates schematically the concept of the current invention. A streptavidin-protein A chimeric protein, identified as (X), is used as a linker between biotinylated DNA and antibody-antigen complex resulting in the formation of a specific antigen-antibody-linker-DNA conjugate. The streptavidin-protein A chimera possesses specific binding affinity for both DNA and antibody. Biotinylated DNA is used as a marker. Antigen is bound through its epitope, the antigenic determinant on an antigen, to the paratope on an antibody.

A segment of the attached marker DNA of the antigen-antibody-linker-DNA conjugate can be amplified by polymerase chain reaction (PCR) using appropriate primers. Polymerase chain reaction has enormous amplification capability which allows the production of large amounts of specific DNA products (PCR products), which can be detected with great sensitivity by various methods.

The extremely high sensitivity of polymerase chain reaction for a target sequence of biotinylated DNA, defined by a set of primers, eliminates the generation of false PCR signals derived from other DNA molecules present in samples. The presence of specific polymerase chain reaction products in the sample demonstrates that marker biotinylated DNA molecules are attached specifically to antigan-antibody complexes evidencing the presence of the antigen.

UTILITY

The novel method of the current invention for detection of extremely small amounts of antigen with a high sensitivity is superior to that of any existing antigen detection system using enzymes, fluorochromes, or radioisotopes as a marker. Therefore, smaller amounts of antigen can be detected by the assay and rare antigen molecules in biological or non-biological samples can be readily detected.

In principle, the immuno-PCR technology can be applied to detection of single molecules. No method is currently available which would have the same degree of sensitivity. In addition, the extremely high sensitivity of the immuno-PCR considerably reduces the amounts of antibodies required resulting in reduced assay costs. This is particularly useful when large amounts of specific antibodies are not available.

The sensitivity of immuno-PCR can be controlled by varying one or more key factors, such as the number of amplification cycles and the detection methods for PCR products. This characteristic allows immuno-PCR technology to be applied to a wide range of biological samples, in which the number of antigens varies considerably.

Another advantage of immuno-PCR technology is its simplicity. Immuno-PCR does not include any complex procedures. Thus it allows the development of fully automated assay systems without a loss of sensitivity. This characteristic offers a great promise for applications in clinical diagnostics.

Although DNA is used as a marker in the experiments described above, other nucleic acid molecules such as RNA can be used as the marker upon biotinylation.

Besides the streptavidin-protein A chimera, any molecule, that allows the specific conjugation of a marker DNA to an antibody, can be used. This includes chemical conjugation of a marker DNA to antibody and bispecific antibodies to a primary antibody and a hapten-containing DNA marker.

Using a similar configuration, any antigen molecule, which is efficiently separated from unbound antibody and unbound chimera-nucleic acid conjugates, can be detected by immuno-PCR without the need for modification of the basic procedure. Such antigen molecules include:

i) antigen immobilized on other types of solid supports, such as membranes and beads;

ii) insoluble or insolubilized antigen; or iii) antigen present on the surface of cells or organelles.

Several key factors determine the sensitivity of the system. These include the number of amplification cycles and detection methods for PCR products. By varying one or more of these factors, the overall sensitivity of the system can be controlled systematically.

By using more sets of primers for PCR amplification, multiple PCR products can be generated from a specific DNA marker. Such multiple products increase the accuracy of detection by eliminating false PCR signals generated by contaminated nucleic acids or those present in samples.

By repeating the cycles of binding antibody to its antigen and binding chimera-DNA conjugates to antigen-antibody complexes, many different DNA markers can be attached to different antigen-antibody complexes. By using specific PCR primers for each DNA marker at the PCR amplification step, many different antigens can be simultaneously detected.

Pre-conjugation of nucleic acid makers to antibodies, i.e., use of antibody-chimera-nucleic acid marker conjugates, should decrease background levels of samples containing molecules that can bind protein A. The current invention is particularly useful for diagnostic purposes. The type and quantity of antigen present in the blood and other bodily fluids is detected by the assay of the current invention. The assay can also be useful for detection of immunodeficiencies allergies.

The following examples are intended to illustrate the invention. They are not to be interpreted to limit the invention in any way.

EXAMPLE 1

Detection of Immobilized BSA By Immuno-Polymerase Chain Reaction

This example illustrates a procedure for detection of immobilized BSA by immuno-polymerase chain reaction.

Various amounts (6.4 ng–6.4 ag; $9.6 \times 10^{-22}$ mol) of BSA in 45 µl of 150 mM NaCl, 20 mM Tris-Cl (pH 9.5), 0.02% $NaN_3$, prepared by serial dilutions, were placed in wells of a microtiter plate (Falcon 3911; Becton Dickinson). The microtiter plate was incubated at 4° C. overnight to immobilize BSA molecules on the surface of the wells. The same solution without BSA was used as the control. The wells were briefly washed several times with Tris-buffered saline [TBS;150 mM NaCl, 20 mM Tris-Cl (pH 7.5), 0.02% $NaN_3$]. Then 200 µl of ETBS (TBS plus 0.1 mM EDTA) containing 4.5% non-fat dried milk and 1 mg/ml denatured salmon sperm DNA was added to each well. The microtiter plate was incubated at 37° C. for 80 minutes to block reactable sites on the surface of the wells to avoid non-specific binding in subsequent steps, and then the wells were washed several times with TETBS (TBS plus 0.1 mM EDTA and 0.1% Tween 20). Into each well, 50 µl of TETBS containing 0.45% non-fat dried milk, 0.1 mg/ml denatured salmon sperm DNA, and diluted (8,000-fold) monoclonal antibody against BSA (mouse ascites fluid, IgG2a, clone BSA-33; Sigma) was added. The microtiter plate was incubated at room temperature for 45 minutes to allow the antibody to bind to immobilized BSA molecules. The wells were washed extensively with TETBS to remove unbound antibody molecules, and 50 μl of TETBS containing 0.45% non-fat dried milk, 0.1 mg/ml denatured salmon sperm DNA, and $1.4 \times 10^{-16}$ mol of biotinylated pUC19 conjugated to the streptavidin-protein A chimera, prepared as below, was added to each well. The microtiter plate was incubated at room temperature for 50 minutes to allow the chimera-pUC19 conjugates to bind to the antigen-antibody complexes, and then the wells were washed extensively with TETBS to removed unbound conjugates. The wells were washed briefly with TBS without $NAN_3$, and the microtiter plate was subjected to PCR. After the PCR amplification, each reaction mixture was analyzed by 2% agarose gel electrophoresis.

The chimera-pUC19 conjugate was prepared by mixing the purified chimera and a biotinylated pUC19 at a molar ratio of biotin and biotin-binding site of 1. The resulting conjugates contain four biotinylated pUC19 per chimera, which possesses four biotin binding sites. The biotinylated pUC19 used was a linear 2.67 kb Hind III-Acc I fragment, in which one biotin molecule had been incorporated at its Hind III terminus by a filling-in reaction with T7 DNA polymerase (Sequenase version 2.0; US Biochemical) in the presence of a biotinylated nucleotide (biotin-14-dATP).

Other antigens than BSA are processed in the same way.

EXAMPLE 2

Immuno-Polymerase Chain Reaction

This example illustrates immuno-polymerase chain reaction conditions used for amplification of a segment of a marker DNA of chimera-marker DNA-antibody-antigen complexes.

Polymerase chain reactions were carried out under the following conditions: 50 mM KCl, 10 mM Tris-Cl (pH 8.3 at 20° C.), 1.5 mM $MgCl_2$, 10 μg/ml gelatin, 0.8 mM dNTPS (0.2 mM each), 2 μM primers (bla-1 and bla-2) 1 μM of each, and 50 units/ml Taq DNA polymerase were mixed. Pre-PCR mixtures sterilized by UV irradiation at 254 nm were added to the wells of a microtiter plate (40 μl/well), and light mineral oil sterilized by UV irradiation was layered (20 μl/well) over the reaction mixture. PCR was performed using an automated thermal cycler using the following temperature profile: Initial denaturation was performed at 94° C., for five minutes; denaturation was performed at (94° C., one minute), annealing was performed at 58° C. for one minute, and extension was performed at 72° C. for one minute); 30 cycles of amplification, that is denaturation—annealing and extension, were performed with final extension performed at 72° C. for five minutes. The 30-mer primers, bla-1 and bla-2, hybridized to a segment of the bla gene, and generated a 261 bp fragment upon PCR amplification.

Following the PCR, post-PCR mixtures were analyzed (15 μl of each) by 2% agarose gel electrophoresis, stained with ethidium bromide.

EXAMPLE 3

Detection of Amplified DNA Segments Conjugated To The Streptavidin-Protein A Chimera This example illustrates a method for detection of biotinylated DNA segments conjugated to the streptavidin-protein A chimera further conjugated to antigen-antibody complex. PCR products are analyzed by standard agarose gel electrophoresis.

A PCR amplification reaction mixture obtained in Example 2 (15 μl) was separated on 2.0% agarose gels, and the DNA was stained with ethidium bromide.

EXAMPLE 4

Cross-linking Marker DNA to Insulin

This example illustrates the direct cross-linking of the marker to the target hormone insulin.

The DNA marker is first chemically cross-linked to insulin by methods described in the specification or by methods known in the art. The insulin-marker DNA conjugate is applied to a sample to detect the presence of the insulin receptor. If the insulin receptor is present in the sample, the insulin-marker DNA conjugate binds to the receptor. The segment of the marker DNA, which has been attached to the insulin receptor through insulin (this means that insulin is used as a cross-linker), is amplified by PCR hybridization, detection of label and is detected by appropriate methods.

---

What is claimed:

1. A method for detecting a rare ligand in a sample, said method comprising steps:
   (1) contacting said sample with a conjugate comprising a non-nucleic acid receptor capable of specifically binding said rare ligand and a nucleic acid marker comprising a predetermined nucleotide sequence to form a specifically bound complex of said rare ligand and said conjugate;
   (2) specifically detecting the presence of said nucleic acid maker of said complex,
   wherein the presence of said nucleic acid marker indicates the presence of said rare ligand in said sample.

2. A method according to claim 1 wherein said specifically detecting step comprises amplifying said nucleic acid marker in a polymerase chain reaction.

3. A method according to claim 1 wherein said specifically detecting step comprises extending said nucleic acid with a polymerase.

4. A method according to claim 1 wherein said receptor is non-covalently conjugated to said nucleic acid marker by a bi-specific linker capable of specifically binding both said receptor and said nucleic acid marker.

5. A method according to claim 1 wherein said receptor is non-covalently conjugated to said nucleic acid marked by a bi-specific linker capable of specifically binding both said receptor and said nucleic acid marker, said nucleic acid marker comprises a hapten and said linker specifically binds said nucleic acid marker at said hapten.

6. A method according to claim 1 wherein said receptor is non-covalently conjugated to said nucleic acid marker by a bi-specific linker capable of specifically binding both said receptor and said nucleic acid marker, said nucleic acid marker comprises a hapten and said linker specifically binds said nucleic acid marker at said hapten, and said hapten is biotin.

7. A method according to claim 1 wherein said receptor is an antibody and said ligand is an antigen or hapten.

8. A method according to claim 1 wherein said receptor is an enzyme and said ligand is a substrate or cofactor.

9. A method according to claim 1 wherein said receptor is avidin or streptavidin said ligand is biotin.

10. A method according to claim 1 wherein said receptor is an antigen or hapten and said ligand is an antibody.

11. A method according to claim 1 wherein said receptor is a substrate or cofactor and said ligand is an enzyme.

12. A method according to claim 1 wherein said receptor is biotin and said ligand is avidin or streptavidin.

13. A method for detecting a ligand in a sample, said method comprising steps:
   (1) contacting a sample comprising a ligand with a conjugate comprising a non-nucleic acid receptor capable of specifically binding said ligand and a nucleic acid marker comprising a predetermined nucleotide sequence to form a specifically bound complex of said ligand and said conjugate, wherein said receptor is an antibody and said ligand is an antigen or hapten;
   (2) specifically detecting the presence or absence of said nucleic acid marker of said complex, wherein said specifically detecting step comprises amplifying said nucleic acid marker in a polymerase chain reaction,
   wherein the presence of said nucleic acid marker indicates the presence of said ligand in said sample.

14. A method according to claim 13 wherein said receptor is non-covalently conjugated to said nucleic acid marker by a bi-specific linker capable of specifically binding both said receptor and said nucleic acid marker.

* * * * *